(12) United States Patent
Huh et al.

(10) Patent No.: US 7,687,259 B2
(45) Date of Patent: *Mar. 30, 2010

(54) METHOD FOR NONCOVALENTLY IMMOBILIZING A BIOMOLECULE ON A SOLID SUBSTRATE AND MICROARRAY PRODUCED ACCORDING TO THE METHOD

(75) Inventors: Nam Huh, Seoul (KR); Jong-myeon Park, Seoul (KR)

(73) Assignee: Samsung Electronics Co., Ltd. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 12/145,921

(22) Filed: Jun. 25, 2008

(65) Prior Publication Data

US 2008/0280782 A1 Nov. 13, 2008

Related U.S. Application Data

(63) Continuation of application No. 11/052,345, filed on Feb. 7, 2005, now Pat. No. 7,611,889.

(30) Foreign Application Priority Data

Feb. 16, 2004 (KR) ............... 10-2004-0009942

(51) Int. Cl.
C12M 1/34 (2006.01)
C12Q 1/68 (2006.01)
G01N 33/53 (2006.01)
C07K 1/10 (2006.01)

(52) U.S. Cl. ............... 435/287.2; 435/6; 435/7.92; 530/402; 530/405

(58) Field of Classification Search ............... None
See application file for complete search history.

(56) References Cited

U.S. PATENT DOCUMENTS

| | | | |
|---|---|---|---|
| 5,143,854 A | 9/1992 | Pirrung et al. | |
| 5,338,614 A | 8/1994 | Bartz et al. | |
| 5,424,186 A | 6/1995 | Fodor | |
| 5,445,934 A | 8/1995 | Fodor et al. | |
| 5,451,683 A | 9/1995 | Barrett et al. | |
| 5,622,826 A | 4/1997 | Varma | |
| 5,744,305 A | 4/1998 | Fodor | |
| 5,900,461 A | 5/1999 | Harris | |
| 6,361,671 B1 | 3/2002 | Mathies et al. | |
| 6,808,908 B2 | 10/2004 | Yao et al. | |
| 2003/0096232 A1 | 5/2003 | Kris et al. | |
| 2003/0108917 A1 | 6/2003 | Huh et al. | |

FOREIGN PATENT DOCUMENTS

| | | |
|---|---|---|
| DE | 19602300 | 7/1997 |
| EP | 1026259 A1 | 9/2000 |
| JP | 2003248000 | 9/2003 |
| JP | 2003528301 | 9/2003 |
| WO | 0106011 | 1/2001 |
| WO | 03066896 | 8/2003 |

OTHER PUBLICATIONS

Japanese Office Action dated Apr. 3, 2007 for Application No. 2005-038463.
Michael J. Taussig and Ulf Landegren, "Progress in antibody arrays", Targets vol. 2, No. 4, pp. 169-176 (2003).
Michael C. Pirrung, "How to Make a DNA Chip", Angew. Chem. Int. Ed., vol. 41, pp. 1276-1289 (2002).
European Search Report dated Nov. 16, 2005 for Application No. 05003305.
Chinese Office Action, dated Mar. 21, 2007 for Application No. 200510074122.6.

*Primary Examiner*—Shafiqul Haq
(74) *Attorney, Agent, or Firm*—Cantor Colburn LLP (57) ABSTRACT

Provided is a method for noncovalently immobilizing a biomolecule on a solid substrate, including: providing a solid substrate having a first functional group attached thereto, the first functional group having a hydrogen bond donating ability; and reacting a mixture of a compound having a hydrogen bond accepting ability and a biomolecule functionalized with a second functional group, with the surface of the substrate, the second functional group having a hydrogen bond donating ability, in order to noncovalently immobilize the biomolecule on the substrate.

4 Claims, 3 Drawing Sheets

SEQUENCE LISTING

<160> NUMBER OF SEQ ID NOS: 26

<210> SEQ ID NO 1
<211> LENGTH: 14
<212> TYPE: DNA
<213> ORGANISM: Artificial Sequence
<220> FEATURE:
<223> OTHER INFORMATION: wild type probe nucleotide

<400> SEQUENCE: 1
ctcctggaag ggca                                              14

<210> SEQ ID NO 2
<211> LENGTH: 14
<212> TYPE: DNA
<213> ORGANISM: Artificial Sequence
<220> FEATURE:
<223> OTHER INFORMATION: mutant type probe nucleotide

<400> SEQUENCE: 2
agctcctaga aggg                                              14

<210> SEQ ID NO 3
<211> LENGTH: 17
<212> TYPE: DNA
<213> ORGANISM: Artificial Sequence
<220> FEATURE:
<223> OTHER INFORMATION: wild type probe nucleotide

<400> SEQUENCE: 3
aggcatactc attgtca                                           17

<210> SEQ ID NO 4
<211> LENGTH: 17
<212> TYPE: DNA
<213> ORGANISM: Artificial Sequence
<220> FEATURE:
<223> OTHER INFORMATION: mutant type probe nucleotide

<400> SEQUENCE: 4
aggcatactg attgtca                                           17

<210> SEQ ID NO 5
<211> LENGTH: 13
<212> TYPE: DNA
<213> ORGANISM: Artificial Sequence
<220> FEATURE:
<223> OTHER INFORMATION: wild type probe nucleotide

<400> SEQUENCE: 5
ccaaagcggc cac                                               13

```
<210> SEQ ID NO 6
<211> LENGTH: 13
<212> TYPE: DNA
<213> ORGANISM: Artificial Sequence
<220> FEATURE:
<223> OTHER INFORMATION: mutant type probe nucleotide

<400> SEQUENCE: 6
ccaaagtggc cac                                                          13

<210> SEQ ID NO 7
<211> LENGTH: 14
<212> TYPE: DNA
<213> ORGANISM: Artificial Sequence
<220> FEATURE:
<223> OTHER INFORMATION: wild type probe nucleotide

<400> SEQUENCE: 7
acgatgacgt tggt                                                         14

<210> SEQ ID NO 8
<211> LENGTH: 14
<212> TYPE: DNA
<213> ORGANISM: Artificial Sequence
<220> FEATURE:
<223> OTHER INFORMATION: mutant type probe nucleotide

<400> SEQUENCE: 8
acgatgatgt tggt                                                         14

<210> SEQ ID NO 9
<211> LENGTH: 13
<212> TYPE: DNA
<213> ORGANISM: Artificial Sequence
<220> FEATURE:
<223> OTHER INFORMATION: wild type probe nucleotide

<400> SEQUENCE: 9
tgggggatgg cag                                                          13

<210> SEQ ID NO 10
<211> LENGTH: 13
<212> TYPE: DNA
<213> ORGANISM: Artificial Sequence
<220> FEATURE:
<223> OTHER INFORMATION: mutant type probe nucleotide

<400> SEQUENCE: 10
gggggacggc aga                                                          13

<210> SEQ ID NO 11
<211> LENGTH: 24
<212> TYPE: DNA
<213> ORGANISM: Artificial Sequence
<220> FEATURE:
<223> OTHER INFORMATION: primer

<400> SEQUENCE: 11
cagcaacaca acatccccca gagg                                              24

<210> SEQ ID NO 12
<211> LENGTH: 25
<212> TYPE: DNA
<213> ORGANISM: Artificial Sequence
<220> FEATURE:
<223> OTHER INFORMATION: primer
```

-continued

```
<400> SEQUENCE: 12
tacagcaacc accaaggcca aatct                                              25

<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
gggcctgggc agtccgatga t                                                  21

<210> SEQ ID NO 14
<211> LENGTH: 25
<212> TYPE: DNA
<213> ORGANISM: Artificial Sequence
<220> FEATURE:
<223> OTHER INFORMATION: primer

<400> SEQUENCE: 14
aggggagggt tcctgggtct gtgta                                              25

<210> SEQ ID NO 15
<211> LENGTH: 25
<212> TYPE: DNA
<213> ORGANISM: Artificial Sequence
<220> FEATURE:
<223> OTHER INFORMATION: primer

<400> SEQUENCE: 15
agaatgtttg cagcgagggg tgtcc                                              25

<210> SEQ ID NO 16
<211> LENGTH: 25
<212> TYPE: DNA
<213> ORGANISM: Artificial Sequence
<220> FEATURE:
<223> OTHER INFORMATION: primer

<400> SEQUENCE: 16
agcggcccta ggatcatctc aaaag                                              25

<210> SEQ ID NO 17
<211> LENGTH: 25
<212> TYPE: DNA
<213> ORGANISM: Artificial Sequence
<220> FEATURE:
<223> OTHER INFORMATION: primer

<400> SEQUENCE: 17
atgcccatct ccaacccaca actca                                              25

<210> SEQ ID NO 18
<211> LENGTH: 25
<212> TYPE: DNA
<213> ORGANISM: Artificial Sequence
<220> FEATURE:
<223> OTHER INFORMATION: primer

<400> SEQUENCE: 18
gcagggaaaa gtgaccaagc caata                                              25

<210> SEQ ID NO 19
<211> LENGTH: 21
```

```
<212> TYPE: DNA
<213> ORGANISM: Artificial Sequence
<220> FEATURE:
<223> OTHER INFORMATION: primer

<400> SEQUENCE: 19
gcagccatga acggcgagga g                                             21

<210> SEQ ID NO 20
<211> LENGTH: 23
<212> TYPE: DNA
<213> ORGANISM: Artificial Sequence
<220> FEATURE:
<223> OTHER INFORMATION: primer

<400> SEQUENCE: 20
aggtaaggcg gccgggtgag aac                                           23

<210> SEQ ID NO 21
<211> LENGTH: 23
<212> TYPE: DNA
<213> ORGANISM: Artificial Sequence
<220> FEATURE:
<223> OTHER INFORMATION: primer

<400> SEQUENCE: 21
aggtaaggcg gccgggtgag aac                                           23

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
tgtggcgacg cgctaaggcc ag                                            22

<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
ggcagggtgg gagggagaa c                                              21

<210> SEQ ID NO 24
<211> LENGTH: 22
<212> TYPE: DNA
<213> ORGANISM: Artificial Sequence
<220> FEATURE:
<223> OTHER INFORMATION: primer

<400> SEQUENCE: 24
gcgtcagggt gcagtgggat gt                                            22

<210> SEQ ID NO 25
<211> LENGTH: 15
<212> TYPE: DNA
<213> ORGANISM: Artificial Sequence
<220> FEATURE:
<223> OTHER INFORMATION: probe nucleotide

<400> SEQUENCE: 25
```

```
                                              -continued
tgttctcttg tcttg                                                       15

<210> SEQ ID NO 26
<211> LENGTH: 14
<212> TYPE: DNA
<213> ORGANISM: Artificial Sequence
<220> FEATURE:
<223> OTHER INFORMATION: probe nucleotide

<400> SEQUENCE: 26
cagctggctc agtt                                                        14
```

METHOD FOR NONCOVALENTLY IMMOBILIZING A BIOMOLECULE ON A SOLID SUBSTRATE AND MICROARRAY PRODUCED ACCORDING TO THE METHOD

CROSS REFERENCE TO RELATED APPLICATIONS

This application is a continuation of U.S. patent application Ser. No. 11/052,345 filed Feb. 7, 2005, which claims the benefit of Korean Patent Application No. 10-2004-0009942, filed Feb. 16, 2004, in the Korean Intellectual Property Office, the disclosure of each of which is incorporated herein in its entirety by reference.

BACKGROUND OF THE INVENTION

1. Field of the Invention

The present invention relates to a method for immobilizing a biomolecule on a solid substrate, and more particularly, to a method for noncovalently immobilizing a biomolecule on a solid substrate.

2. Description of the Related Art

The term "microarray" refers to a substrate in which specific molecules are densely immobilized in a predetermined region. Examples of the microarray include, for example, a polynucleotide microarray and a protein microarray. The term "polynucleotide microarray" refers to a substrate on which polynucleotides are densely immobilized in each predetermined region. The microarray is well known in the art, for example, U.S. Pat. Nos. 5,445,934 and 5,744,305.

A polynucleotide is immobilized on a solid substrate by synthesizing a polynucleotide directly on a substrate or by immobilizing a polynucleotide previously synthesized at a predetermined location on a substrate (spotting method). Polynucleotide microarrays and methods of producing the same are described in U.S. Pat. Nos. 5,744,305, 5,143,854 and 5,424,186, the disclosures of which are incorporated herein in their entirety by reference. The spotting method is widely used to covalently immobilize a biomolecule on a solid substrate. For example, a biomolecule is generally immobilized on a solid substrate by activating a surface of the substrate with a nucleophilic functional group, such as an amino group, to which a biomolecule, for example, a polynucleotide, activated with a good leaving group is coupled, and then removing unreacted reactants from the substrate. A method for noncovalently immobilizing a biomolecule on a substrate has not been known in the art.

Polyethylene glycol, a hydrophilic compound, has been used in a microarray. Polyethylene glycol was attached to both ends of a DNA strand via a covalent bond and the DNA strand was immobilized on a substrate to obtain a microarray [*Journal of Experimental hematology* 2003: 11(4): 393-397]. US-2003-0108917-A1 describes a method of producing a microarray by immobilizing a probe polynucleotide on a hydrogel comprised of a star-like polyethylene glycol derivative having an epoxy group at its terminal.

However, in these methods, the biomolecule is covalently immobilized on the substrate. That is, the substrate or the biomolecule should have a reactive functional group attached thereto. In addition, a covalent bond may be formed in severe reaction conditions. Further, it is difficult to control the reaction conditions and the operation is complicated. Furthermore, unreacted reactive substances must be removed after the completion of the reaction.

The present inventors conducted research and discovered a method for noncovalently immobilizing a biomolecule on a solid substrate, the method providing a microarray having a strong quality to be efficiently used in an analysis of a target molecule.

SUMMARY OF THE INVENTION

The present invention provides a method for noncovalently immobilizing a biomolecule on a solid substrate.

The present invention also provides a microarray produced according to the above method.

According to an aspect of the present invention, there is provided a method for noncovalently immobilizing a biomolecule on a solid substrate, comprising: providing a solid substrate having a first functional group attached thereto, the first functional group having a hydrogen bond donating ability; and reacting a mixture of a compound having a hydrogen bond accepting ability and a biomolecule functionalized with a second functional group, with the surface of the substrate, the second functional group having a hydrogen bond donating ability, in order to noncovalently immobilize the biomolecule on the substrate.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

According to an embodiment of the present invention, there is provided a method for noncovalently immobilizing a biomolecule on a solid substrate, comprising: providing a solid substrate having a first functional group attached thereto, the first functional group having a hydrogen bond donating ability; and reacting a mixture of a compound having a hydrogen bond accepting ability and a biomolecule functionalized with a second functional group, with the surface of the substrate, the second functional group having a hydrogen bond donating ability, in order to noncovalently immobilize the biomolecule on the substrate.

The first functional group having a hydrogen bond donating ability and the second functional group having a hydrogen bond donating ability may be different or identical. The first functional group having a hydrogen bond donating ability and the second functional group having a hydrogen bond donating ability may be respectively selected from the group consisting of an amino group, a thiol group and a hydroxyl group, but are not limited thereto. Specific examples of the compound having an amino group include, but are not limited to, γ-aminopropyltriethoxysilane (GAPS), γ-aminopropyltdiethoxysilane (GAPDES), and aminohexyl group. A compound having the first functional group can be derived by introducing the first functional group, such as an amino group, a thiol group, and a hydroxyl group, into a coating material, such as acetylchloride silane, anhydrous silane, sulfonylchloride silane, and isothiocyanate silane. This introduction process is well known in the art and an ordinary person in the art can easily perform this process.

In the embodiment of the present invention, the compound having a hydrogen bond accepting ability refers to a molecule which contains an atom of high electronegativity, such as nitrogen, oxygen, and sulfur, and thus may donate an electron necessary to form a hydrogen bond. Examples of the compound include polyethylene glycol (PEG) or its derivative and polyethyleneimine or its derivative. In addition, PEG or its derivative, or polyethyleneimine or its derivative may be used in a concentration of 0.4 to 6.0 mM respectively, and may have a molecular weight of 200 to 1,000,000 Da, preferably 200 to 100,000 Da, and more preferably 200 to 10,000 Da. In an exemplary embodiment of the present invention, PEG is used in a concentration of 6.0 mM and has a molecular weight of 10,000 Da.

In the embodiment of the present invention, the solid substrate is not specifically limited and may be any solid substrate that can provide a surface. The solid substrate may be formed of plastic materials, such as polyethylene, polypropylene, polystyrene, and polyurethane, glass, silicon wafer, and their modification. The solid substrate may have the first functional group in itself or by a chemical or physical treatment, such as coating.

The biomolecule is a compound originated from an organism or a synthetic compound thereof. The biomolecule may be selected from the group consisting of a nucleic acid, a protein, a polysaccharide, and a combination thereof. Preferably, the biomolecule is a nucleic acid. Examples of the nucleic acid may include DNA and RNA. In general, the biomolecule to be immobilized on the solid substrate specifically reacts with a target molecule to be analyzed. For example, a nucleic acid may specifically react with a target nucleic acid having a complementary nucleotide sequence via hybridization reaction. A protein may specifically react with a target molecule via an antigen-antibody reaction, interaction between ligand and receptor, or interaction between an enzyme and a substrate. A polysaccharide may be specifically recognized by an antibody or a protein, such as lectin, able to recognize a polysaccharide. By using a detection system which may detect the specific interaction between the biomolecule and the target molecule, a microarray produced according to the present method can be used in various analyses.

The concentration of the biomolecule used in immobilization may vary depending on the reaction conditions and the type of data to be obtained. That is, the concentration of the biomolecule is not specifically limited. In an exemplary embodiment of the present invention, a concentration of DNA may be in a range of 20 to 100 μM, but are not limited thereto.

The immobilization method according to the embodiment of the present invention can be applied to the conventional methods for producing a DNA or protein microarray. One of the conventional methods is a method of producing a microarray using photolithography. This photolithographic method includes coating a surface of a substrate with a monomer protected with a removable protecting group, exposing a predetermined region of the surface to an energy source to remove the protecting group, and coupling a second monomer protected with a removable protecting group to the monomer, and repeating the above exposing and coupling, thereby producing a polynucleotide microarray (photolithographic method). In this method, a polynucleotide is synthesized by extending monomers one by one, thus allowing for immobilization of a polynucleotide. In a method of producing a microarray by spotting, a polynucleotide previously synthesized is immobilized in a predetermined region on a substrate.

These methods of producing a microarray are described, for example, in U.S. Pat. Nos. 5,744,305, 5,143,854 and 5,424,186. The disclosures of these patents are incorporated herein in their entirety by reference, in which polynucleotide microarrays and methods of producing the same are described.

According to another embodiment of the present invention, there is provided a microarray produced according to the above method.

The present invention will be described in more detail by presenting examples. These examples are for illustrative purpose, and are not intended to limit the scope of the present invention.

EXAMPLE

Example 1

Production of a DNA Microarray by Reacting a Mixture of Polyethylene Glycol (PEG) and a DNA Functionalized with an Amino Group at its 5' end with a Surface of a Glass Substrate Coated with an Amino Group In this Example, a mixture of PEG and a DNA functionalized with an amino group at its 5' end was reacted with a surface of a glass substrate coated with γ-aminopropyltriethoxysilane (GAPS) to produce a DNA microarray having DNAs arranged in spots.

First, Cat no. 40004, available from Dow Coring (www.corning.com) was used as the glass substrate coated with GAPS. Probe nucleotides functionalized with an aminohexyl group at their 5' ends (SEQ ID Nos. 1 to 10) were respectively dissolved at a concentration of 20 μM in a solution of 6 mM PEG (available from Aldrich, Mw 10,000) in 0.1 M NaHCO$_3$ (pH 9) containing 50% DMSO. Probe polynucleotides to be immobilized were composed of a perfect match sequence (wild-type probes) that are complementary to a specific region of exons 7 to 10 in a gene of maturity-onset diabetes of the young, MODY 1, and mismatch sequences (mutant-type probes) that are complimentary to the sequence of wild-type probe except for one nucleotide.

TABLE 1

Names and SEQ ID Nos. of the probe polynucleotides

| Probe location | Wild-type probe sequence | Mutant-type probe sequence |
| --- | --- | --- |
| MO1E07-02rwp1 | SEQ ID No. 1 | SEQ ID No. 2 |
| MO1E07-03rwp1 | SEQ ID No. 3 | SEQ ID No. 4 |
| MO1E08-01rwp1 | SEQ ID No. 5 | SEQ ID No. 6 |
| MO1E09-01rwp1 | SEQ ID No. 7 | SEQ ID No. 8 |
| MO1E10-01rwp1 | SEQ ID No. 9 | SEQ ID No. 10 |

The obtained probe polynucleotide solutions were respectively spotted at 500 μl per spot on the glass substrate, using Pix5500 Spotter™ (available from Cartesian). Then, the immobilization reaction was performed at 70° C. and 30% humidity for one hour in a constant temperature and humidity chamber. After the completion of the reaction, the glass substrate was washed with distilled water and residual amino groups on the substrate were protected with anhydrous succinic acid (blocking agent). Then, the glass substrate was washed with ethanol and spin-dried to obtain a microarray having the probe polynucleotide which was immobilized. The obtained microarrays respectively had sixty spots arranged with intervals of 300 μm therebetween.

Example 2

Analysis of the Target Nucleic Acid Using a Microarray Produced According to the Method of the Embodiment of the Present Invention In this Example, hybridization reactions between the probe polynucleotide and the target nucleic acid were carried out using the probe polynucleotide microarrays produced in Example 1, and then based on the results of hybridization, the qualities of microarrays produced according to the method of the embodiment of the present invention were estimated.

First, the target DNAs were amplified. A PCR was performed using fourteen oligonucleotides having SEQ ID Nos. 11 to 24, respectively, as a primer and gDNA isolated from human blood as a template to obtain polynucleotides containing exons 7 to 10 of MODY 1.

The conditions of the PCR were as follows: 0.2 µl wild-type genome DNA, each 200 µM of dATP, dGTP, dCTP, 40 µM dTTP, 160 µM Cy3-labeled dUTP (Amersham Biosciences, Uppsala, Sweden), and 200 nM of ten multiple PCR sets corresponding ten regions of exons and promoters were mixed together. Then, 40 cycles of PCR was performed with one cycle including denaturation at 95° C. for 30 sec, annealing at 64° C. for 10 sec, and extension at 72° C. for 3 minutes. The resulting PCR products were purified using a Qiagen kit, and then those having a ratio of $A_{260}/A_{550}$ of 1.0 to 3.5 were selected for the subsequent process.

The purified PCR products were fragmented with 0.5 U DNase I (Boehringer Mannheim, Mannheim, Germany) at 37° C. for 10 minutes. Then, a stop mix (20 mM EDTA, pH 8.0-1% SDS-0.2 M NaCl) was added to the products to stop the DNase I digestion reaction. Next, the fragmented products were adjusted to a concentration of 150 to 187.5 nM and denatured at 94° C.° for 5 minutes and placed on ice for 2 minutes for cooling. The products were respectively mixed with the same amount of a hybridization buffer (6×SSPE-0.1% Triton X-100), and then applied to the microarrays obtained from Example 1. The microarrays were respectively incubated at 32° C. for 12 to 16 hours and then washed with a wash buffer I (6×SSPE-Triton X-100 0.005%) for 5 minutes and then a wash buffer II (3×SSPE-Triton X-100 0.005%) for 5 minutes. Subsequently, the microarrays were dried at room temperature for 15 minutes, and imaged using GenePix 4000B Scanner™ (Axon Instruments) at 532 nm. The obtained images were analyzed using GenePix Pro Software™ (Axon Instruments, Union City, Calif.).

Figure 1:
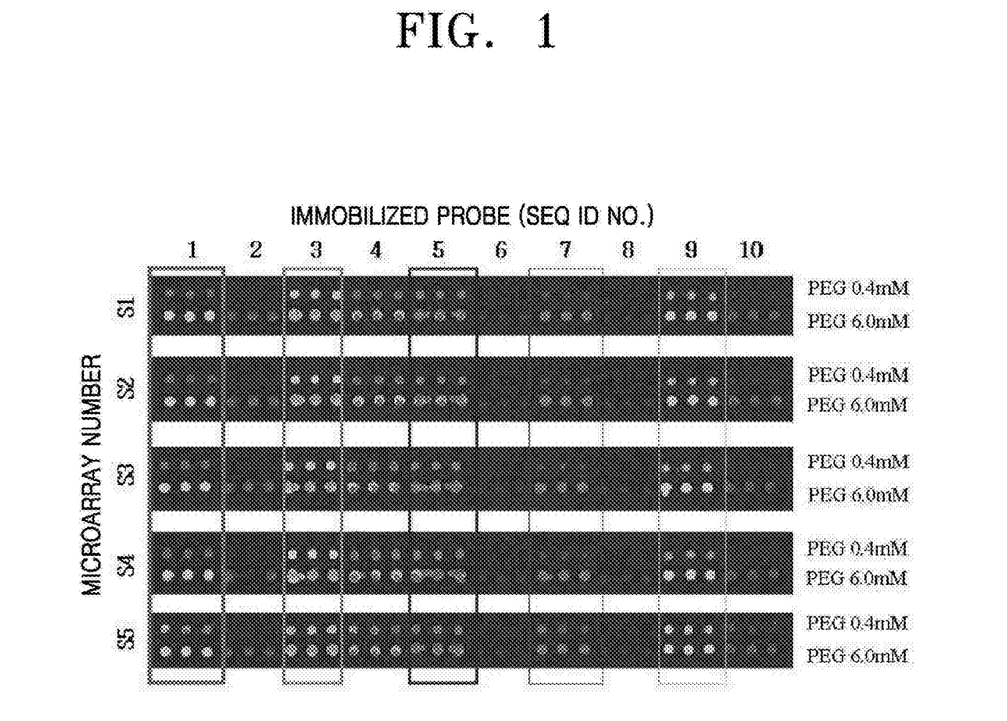
FIGS. 1 through 3 are views illustrating results of fluorescent measurements for the microarrays produced using polyethylene glycol (PEG) in a concentration of 0.4 mM and 6.0 mM, respectively.

The analytical results are shown in FIG. 1 and Table 2. Experiments were performed for five microarrays, each microarray having the wild-type and mutant-type probes as listed in Table 1 immobilized thereon (three spots for each probe). The obtained image and fluorescence intensity data are shown in FIG. 1 and Table 2. FIG. 1 illustrates fluorescence image scanned for the five microarrays S1 through S5 having probe polynucleotides immobilized thereon (obtained in Example 1), of which SEQ ID Nos. are respectively designated in the upper portion of FIG. 1, after hybridization with the target nucleic acid on each microarray. In FIG. 1, spots in an upper row and spots in a lower row in each microarray corresponded to concentrations of PEG at 0.4 mM and 6.0 mM, respectively. Table 2 shows fluorescence intensity measured at 532 nm for the spots in FIG. 1. Spots obtained using a concentration of PEG at as low as 0.4 mM were used as controls were used as controls, since it is difficult to obtain the spots having a similar density of immobilized probe nucleotides to that of the spots obtained using a concentration of PEG at 6.0 mM.

TABLE 2

Comparison of fluorescence intensities according to a PEG concentration used in probe immobilization

| Number of microarray | Immobilized probe (SEQ ID Nos.) | | | | | | | | | | Total average | |
|---|---|---|---|---|---|---|---|---|---|---|---|---|
| | 1 | | 3 | | 5 | | 7 | | 9 | | | |
| | 0.4 mM | 6.0 mM | 0.4 mM | 6.0 mM | 0.4 mM | 6.0 mM | 0.4 mM | 6.0 mM | 0.4 mM | 6.0 mM | 0.4 mM | 6.0 mM |
| S1 | 1510 | 6846 | 1407 | 8493 | 1603 | 8202 | 1208 | 8157 | 2229 | 7534 | 1591 | 7846 |
| S2 | 8572 | 16457 | 7281 | 18076 | 7464 | 20056 | 5792 | 17397 | 12938 | 16744 | 8410 | 17746 |
| S3 | 678 | 1553 | 679 | 1789 | 766 | 1690 | 672 | 1447 | 943 | 1531 | 747 | 1602 |
| S4 | 290 | 611 | 284 | 658 | 285 | 551 | 238 | 592 | 396 | 583 | 299 | 599 |
| S5 | 2295 | 5850 | 2131 | 7245 | 2205 | 5464 | 1943 | 6156 | 3257 | 5660 | 2366 | 6075 |
| Average | 2669 | 6264 | 2356 | 7252 | 2464 | 7193 | 1971 | 6750 | 3953 | 6410 | 2683 | 6774 |

As shown Table 2, the fluorescence intensity of the spots on the microarray obtained using a concentration of PEG at 6.0 mM was 6774, while that of the spots on the microarray obtained using a concentration of PEG at 0.4 mM was 2683. In addition, a ratio of the fluorescence intensities of the spots on the microarray obtained using a concentration of PEG at 6.0 mM to fluorescence intensity of the spots on the microarray obtained using a concentration of PEG at 0.4 mM was 2.87. Thus, when a microarray is produced according to the embodiment of the present invention, the fluorescence intensity is directly proportional to the concentration of PEG used. That is, the case using a concentration of PEG at 6.0 mM can obtain about a 3 fold higher fluorescence intensity than the case using a concentration of PEG at 0.4 mM. Thus, it was confirmed that the sensitivity of the fluorescence intensity can be increased by immobilizing probes using PEG. The proportional relation between the PEG concentration and the fluorescence intensity was kept up to a concentration of PEG at 8 mM, above which a pin hole was blocked during spotting, thus preventing practical use (data not shown).

To confirm that in analysis of the target nucleic acid using a microarray produced according to the method of the embodiment of the present invention, the probes can specifically react with the target nucleic acid, the ratios of fluorescence intensity of the wild-type probe (wp) to the fluorescence intensity of the mutant-type probe (mp) were obtained. The results are shown in Table 3.

TABLE 3

Ratios of fluorescence intensity of the wild-type probe (wp) to fluorescence intensity of the mutant-type probe (mp)

| | Ratio of fluorescence intensities | | | | | | | | | | |
|---|---|---|---|---|---|---|---|---|---|---|---|
| | SEQ ID Nos. 1/2 | | SEQ ID Nos. 3/4 | | SEQ ID Nos. 5/6 | | SEQ ID Nos. 7/8 | | SEQ ID Nos. 9/10 | | Total average |
| Number of microarray | 0.4 mM | 6.0 mM | 0.4 mM | 6.0 mM | 0.4 mM | 6.0 mM | 0.4 mM | 6.0 mM | 0.4 mM | 6.0 mM | 0.4 mM | 6.0 mM |
| S1 | 10.76 | 17.26 | 9.84 | 20.13 | 10.73 | 18.23 | 9.15 | 21.08 | 12.69 | 20.00 | 10.63 | 19.34 |
| S2 | 7.33 | 7.76 | 6.79 | 7.77 | 6.86 | 8.74 | 6.38 | 8.17 | 6.91 | 7.44 | 6.85 | 7.98 |
| S3 | 6.69 | 8.91 | 6.88 | 8.56 | 7.56 | 7.63 | 7.17 | 6.87 | 8.42 | 9.98 | 7.34 | 8.39 |
| S4 | 3.06 | 3.38 | 3.14 | 3.38 | 2.96 | 2.59 | 2.57 | 2.69 | 3.99 | 3.73 | 3.14 | 3.15 |
| S5 | 11.71 | 16.20 | 12.64 | 18.75 | 12.00 | 16.28 | 12.81 | 17.28 | 12.20 | 15.94 | 12.27 | 16.89 |
| Average | 7.91 | 10.70 | 7.86 | 11.72 | 8.02 | 10.69 | 7.62 | 11.22 | 8.84 | 11.42 | 8.05 | 11.15 |

A ratio of the fluorescence intensity of the wild-type probe (wp) to the fluorescence intensity of the mutant-type probe (mp), i.e., wp/mp was 8.05 for the spots using a concentration of PEG at 0.4 mM, while said ratio was 11.15 for the spots using a concentration of PEG at 6.0 mM, being about 1.31 fold higher than the above ratio 8.05. This demonstrates that the target nucleic acid can be detected with increased specificity, as the concentration of PEG used to immobilize the probe nucleotides becomes higher.

From the results in Examples 1 and 2, using a method for noncovalently immobilizing a probe nucleotide on a glass substrate in a simple manner, a microarray having high analytical sensitivity and specificity can be provided, even without using a conventional method for covalently immobilizing a probe nucleotide on a glass substrate.

Example 3

The Effect of PEG Concentration on a Microarray

In this Example, a probe nucleotide array was produced and hybridization reaction was performed in the same manner as in Examples 1 and 2, except that a sequence of probe nucleotide to be immobilized was changed. The probe nucleotide had SEQ ID No. 25 and a target polynucleotide had a perfectly matched polynucleotide sequence to SEQ ID No. 25.

Figure 2:
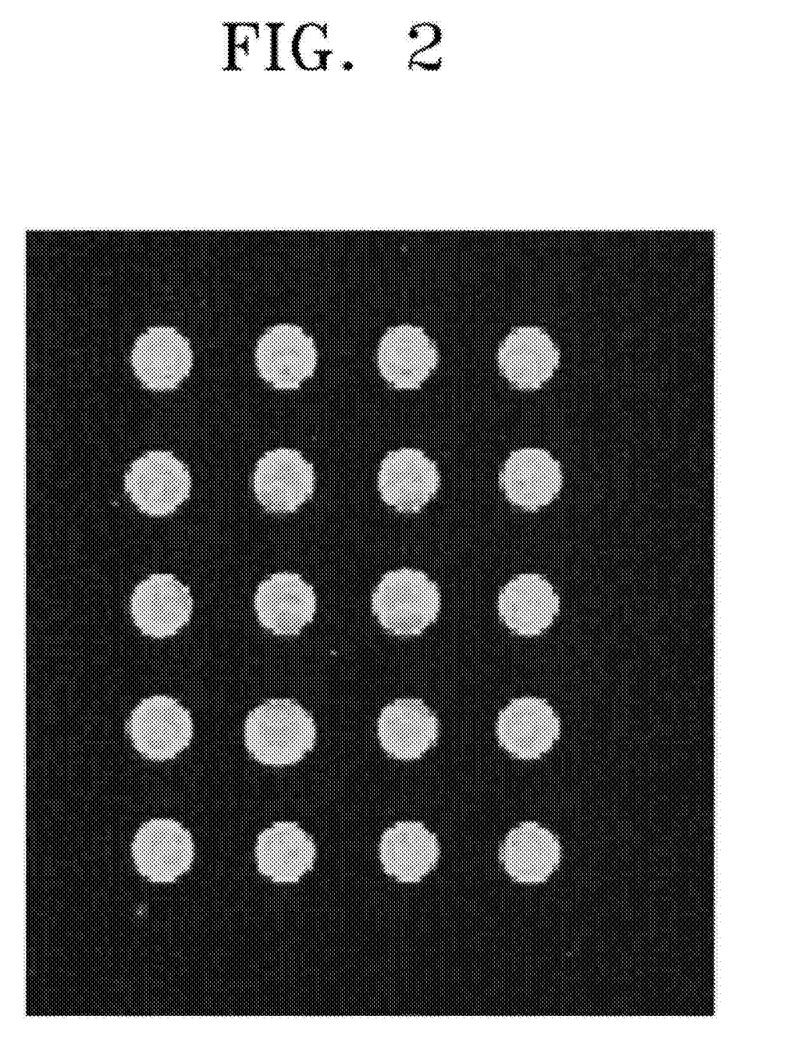
Figure 3:
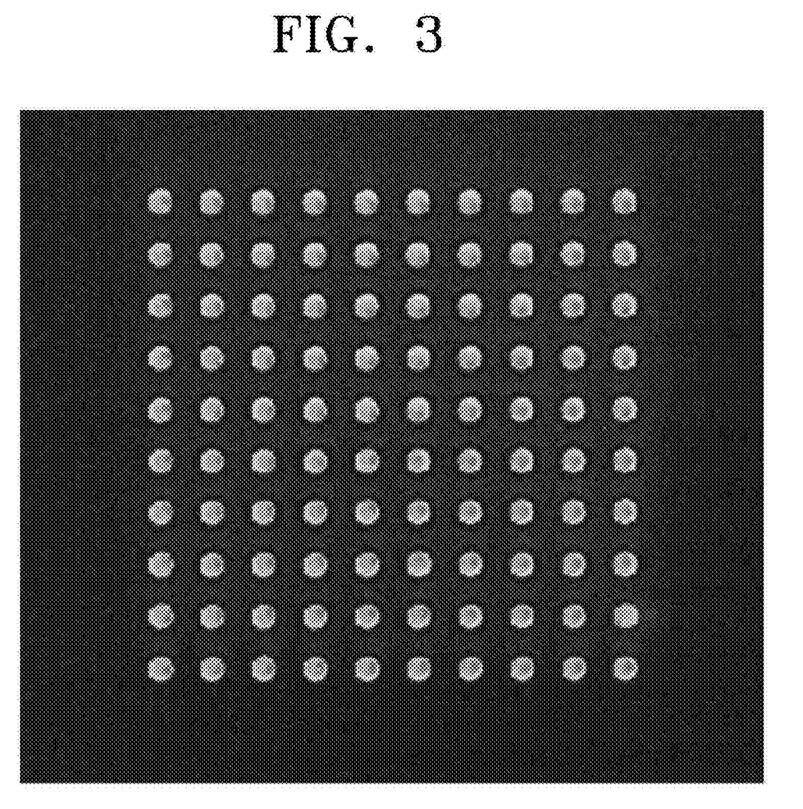

As a result, the fluorescence intensity of the spots on the microarray obtained using a concentration of PEG at 0.4 mM was 7,700, while that of the spots on the microarray obtained using a concentration of PEG at 6.0 mM was 15,000. FIGS. 2 and 3 are views illustrating the results of fluorescent measurement for the microarrays produced using PEG in a concentration of 0.4 mM and 6.0 mM, respectively.

This demonstrates that as the concentration of PEG used to immobilize the probe nucleotides becomes higher, the fluorescence intensity detected becomes higher.

Example 4

Production of a DNA Microarray by Reacting a Mixture of PEG and a DNA Functionalized with an Amino Group at its 5' End with a Surface of a Silicon Wafer In this Example, microarrays were produced in the same manner as in Example 1, except that a silicon wafer (available from LG Siltron: a P-type silicon wafer doped with boron) coated with GAPS was used as a solid substrate. Then, hybridization with a target nucleic acid was performed on each microarray and the fluorescence intensity was measured in the same manner as in Example 2. The same probe and target polynucleotides as in Example 3 were used.

Coating of GAPS on the silicon wafer was performed as follows. A solution of GAPS in ethanol (20% (v/v)) was spin-coated on the silicon wafer using spin coater model CEE 70™ (available from CEE). The spin coating process comprised an initial coating at 500 rpm/10 sec and a main coating at 2,000 rpm/10 sec. After the completion of the spin-coating, the substrate was fixed on a Teflon wafer carrier to be cured at 120° C. for 40 minutes. Then, the substrate was dipped in water for 10 minutes, sonicated for 15 minutes for washing, and again dipped in water for 10 minutes. Next, the substrate was spin-dried. After drying, the substrate was cut into a square or rectangular form for experiment. All experiments were carried out in a clean room-class 1,000 from which most dust particles had been removed.

Figure 4:
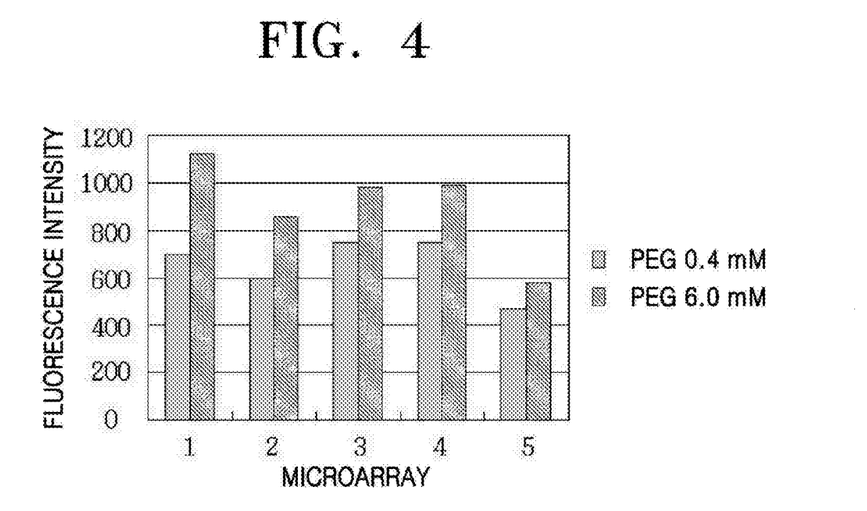
FIG. 4 is a graph illustrating fluorescence intensity for the microarray having a probe polynucleotide immobilized on a silicon wafer produced using the method according to an embodiment of the present invention and for control microarray.

The results of fluorescence intensity are shown in FIG. 4. FIG. 4 is a graph illustrating the fluorescence intensity for the microarray having a probe polynucleotide immobilized on a silicon wafer using PEG in a concentration of 0.4 mM and 6.0 mM, respectively. As illustrated in FIG. 4, it was confirmed that a high fluorescence intensity can be obtained even by noncovalently immobilizing a probe on a substrate using PEG and the fluorescence intensity was proportional to the concentration of PEG used.

Example 5

The Effect of a Concentration of Probe Polynucleotide on Fluorescence Intensity

In this Example, a probe nucleotide array was produced and a hybridization reaction and measurement of a fluorescence intensity were performed in the same manner as in Examples 1 and 2, except that the type and concentration of a probe polynucleotide to be immobilized were changed. The probe polynucleotide having SEQ ID No. 26 was used in a concentration of 20 μM or 100 μM in the immobilization reaction.

The fluorescence intensities were 12,238 and 8,321 in the case using the probe polynucleotide in the concentrations of 20 μM and 100 μM, respectively.

From the result of Example 5, it was confirmed that the optimal fluorescence intensity can be obtained using the probe polynucleotide in a concentration of about 20 μM. In general, when a probe polynucleotide is covalently immobilized, it is used in a concentration above 20 μM. Thus, the method according to the embodiment of the present invention can reduce the amount of probe polynucleotide used in immobilization.

The method for immobilizing a biomolecule on a solid substrate according to the embodiment of the present invention can provide a probe polynucleotide immobilized on a solid substrate without using chemical species having a high reactive functional group. Thus, the present method may provide a simplified process and low costs. In addition, the present method may produce a microarray having good quality in view of sensitivity and specificity of reaction.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of producing a microarray, comprising:
providing a solid substrate having an amino functional group attached thereto;
dissolving a nucleic acid functionalized with an amino group in a solution comprising polyethylene glycol (PEG) to form a solution containing the nucleic acid and the PEG; and
transferring the solution containing the nucleic acid and the PEG to the substrate, in order to noncovalently immobilize the nucleic acid on the substrate via noncovalent intervention of the PEG, wherein a concentration of the PEG is in a range of 0.4 to 8.0 mM.

2. The method of claim 1, wherein the PEG has a molecular weight of 200 to 1,000,000 Da.

3. The method of claim 1, wherein a concentration of the nucleic acid is in a range of 20 to 100 μM.

4. A microarray produced according the method of claim 1.

* * * * *